(12) United States Patent
Choi

(10) Patent No.: US 12,059,514 B2
(45) Date of Patent: Aug. 13, 2024

(54) BREAST PUMP AND BREAST SHIELD USED THEREIN

(71) Applicant: HAENIM CO., LTD., Incheon (KR)

(72) Inventor: Heung Bae Choi, Incheon (KR)

(73) Assignee: HAENIM CO., LTD., Incheon (KR)

( * ) Notice: Subject to any disclaimer, the term of this patent is extended or adjusted under 35 U.S.C. 154(b) by 0 days.

(21) Appl. No.: 16/682,662

(22) Filed: Nov. 13, 2019

(65) Prior Publication Data

US 2021/0093760 A1    Apr. 1, 2021

(30) Foreign Application Priority Data

Sep. 27, 2019  (KR) .................. 10-2019-0119382

(51) Int. Cl.
*A61M 1/06*    (2006.01)

(52) U.S. Cl.
CPC ..... *A61M 1/066* (2014.02); *A61M 2205/3344* (2013.01)

(58) Field of Classification Search
CPC ........ A61M 1/06; A61M 1/062; A61M 1/064; A61M 1/066; A61M 1/068; A61M 1/007; A61M 2210/1007; A61M 1/067; A61M 1/069; A61M 1/0693; A61M 1/06935; A61M 1/0697; A61B 2018/00333; A61J 13/00; A61H 9/0057; A61H 2205/082
See application file for complete search history.

(56) References Cited

U.S. PATENT DOCUMENTS

| 7,666,162 | B2 * | 2/2010 | Renz ...................... | A45C 15/00 |
| | | | | 604/74 |
| 2002/0198489 | A1 * | 12/2002 | Silver ................... | A61M 1/066 |
| | | | | 119/14.47 |
| 2005/0222536 | A1 * | 10/2005 | Silver ................... | A61M 1/064 |
| | | | | 604/74 |
| 2005/0256449 | A1 * | 11/2005 | Tashiro ................. | A61M 1/066 |
| | | | | 604/74 |
| 2008/0287037 | A1 * | 11/2008 | Solberg ................ | A61M 1/067 |
| | | | | 450/36 |

FOREIGN PATENT DOCUMENTS

| JP | 2007-89904 A | 4/2007 |
| KR | 10-2001-0072907 A | 7/2001 |
| KR | 20-2010-0006511 U | 6/2010 |
| KR | 10-1660366 B1 | 9/2016 |
| WO | WO 2018/041365 A1 | 3/2018 |

OTHER PUBLICATIONS

International Search Report mailed Jun. 29, 2020, issued to International Application No. PCT/KR2019/014549.

* cited by examiner

*Primary Examiner* — Shefali D Patel
*Assistant Examiner* — William R Frehe
(74) *Attorney, Agent, or Firm* — Stein IP, LLC

(57) ABSTRACT

The present invention relates to a breast shield used in a breast pump configured to pump human breast milk. The breast shield includes a hard base portion including both ends and a sidewall connecting the both ends to include a hollow in the base portion in which the both ends are open and a human mamma is accommodated in the hollow through any one of the both ends, through holes passing through the sidewall, and a soft portion configured to surround an outer surface and an inner surface of the base portion, prevent an airflow through the through holes, and have flexibility.

4 Claims, 4 Drawing Sheets

BREAST PUMP AND BREAST SHIELD USED THEREIN

CROSS-REFERENCE TO RELATED PATENT APPLICATION

This U.S. non-provisional patent application claims priority under 35 U.S.C. § 119 of Korean Patent Application No. 10-2019-0119382 filed on Sep. 27, 2019 in the Korean Patent Office, the entire contents of which are hereby incorporated by reference.

BACKGROUND OF THE INVENTION

Field of the Invention

The present invention relates to a breast pump and a breast shield used therein, and more particularly, a breast pump capable of massaging a mother's breast and a breast shield used therein.

Discussion of the Related Art

Generally, breast pumps are devices for pumping human breast milk by applying negative pressure to a human's nipple. Breast pumps include a vacuum pump operated by a hand or an electrical motor, at least one breast shield located on a breast, an adapter, and a breast milk collection container in which pumped breast milk is collected. The breast shield is connected to the vacuum pump directly or through a suction fine so that periodically changed negative pressure may be applied to a breast in the breast shield to pump breast milk from the breast. The adapter supports the breast shield and connects the breast shield to the vacuum pump or suction line.

The breast shield includes a funnel and a connection portion configured to be connected to the adapter. The funnel is generally formed to have a conical shape with a hollow formed therein and may be formed to be hard or soft. The connection portion may have a tubular shape.

The breast shield may include a component configured to stimulate a breast. The component massages mammary glands inside the breast so as not to be pushed together in order to provide an effect of effectively discharging breast milk.

A related art for the massage is disclosed in Korean Utility Model Application No. 20-2010-0006511.

However, a soft material is used for massage. Here, when negative pressure is formed therein, a soft part including the soft material shrinks and a gap is formed between the soft part and a hard part such that breast milk flows backward outside an approximately funnel-shaped breast shield and leaks out.

Also, an effect of massaging the breast is high only when a small area of the breast is strongly pressurized with the breast shield while the negative pressure is applied to the inside of the breast shield. However, according to an existing technique, since an entirety of the breast shield shrinks and a pressurizing force is distributed to a large area of the breast when the negative pressure is applied to the inside of the breast shield, the massaging effect is low.

SUMMARY OF THE INVENTION

Accordingly, an object of the present disclosure is to address the above-described and other problems.

Another object of the present invention is to provide a breast pump and a breast shield used therein in which when negative pressure is applied to the inside of the breast shield, a particular part of the breast shield pressurizes and massages a breast.

Another object of the present invention is to provide a breast pump and a breast shield used therein in which when negative pressure is applied to the inside of the breast shield, the negative pressure is not decreased to be lower than a reference value in the breast shield.

Another object of the present invention is to provide a breast pump and a breast shield used therein in which when negative pressure is applied to the inside of the breast shield, breast milk does not leak out of the breast shield.

According to an aspect of the present invention, there is provided a breast shield used in a breast pump configured to pump human breast milk, the breast shield comprising: a base portion including both ends and a sidewall connecting the both ends, wherein a hollow is formed in the base portion, the both ends are open, and a human breast is accommodated in the hollow through one of the both ends; a through hole, passing through the sidewall; and a soft portion, surrounding an outer surface and an inner surface of the base portion, preventing an airflow through the through hole, and having flexibility.

According to another aspect of the present invention, the soft portion may include a first soft layer pressed against the inner surface of the base portion, a second soft layer pressed against the outer surface of the base portion, and a third soft layer provided at each of the through holes and connected to each of the first soft layer and the second soft layer.

According to another aspect of the present invention, the third soft layer may be formed to be convex toward an inside of the base portion.

According to another aspect of the present invention, the third soft layer may elongate and move toward the inside of the base portion when negative pressure is formed in the base portion.

According to another aspect of the present invention, the soft portion may further include a contact edge provided along an edge of an end of the base portion and pressed against the human mamma.

According to another aspect of the present invention, the contact edge may be connected to each of the first soft layer and the second soft layer.

According to another aspect of the present invention, the contact edge may be formed to be convex toward the human mamma to come into contact therewith.

According to another aspect of the present invention, the soft portion may be formed through insertion molding.

According to another aspect of the present invention, there is provided a breast pump comprising: a breast shield formed to be pressed against a human breast; a pressure adjustor configured to adjust a pressure inside the breast shield to pump human breast milk; and a pumped milk storage portion in which pumped breast milk is stored, wherein the breast shield includes a hard base portion having a funnel shape including open both ends and a hollow therein; through holes passing through a sidewall of the base portion; and a soft portion which has flexibility and includes a single layer area covering each of the through holes and a double layer area connected to the single layer area and configured to accommodate the base portion therein.

As described above, according to the embodiment of the present invention, a breast pump and a breast shield used therein provide the following effects.

As a first effect, according to one embodiment of the present invention, when negative pressure is applied to the inside of the breast shield, a particular part of the breast shield may pressurize and massage a breast.

As a second effect, according to one embodiment of the present invention, when negative pressure is applied to the inside of the breast shield, the negative pressure is not decreased to be lower than a reference value in the breast shield.

As a third effect, according to one embodiment of the present invention, when negative pressure is applied to the breast shield, breast milk does not leak out of the breast shield.

BRIEF DESCRIPTION OF THE DRAWINGS

The accompanying drawings, which are included to provide a further understanding of the present invention and are corporate in and constitute a part of this specification, illustrate embodiments of the present invention and together with the description serve to explain the principle of the present invention, in the drawings.

DETAILED DESCRIPTION OF THE EMBODIMENTS

Embodiments which will be described below are merely examples for understanding the present invention, and it should be understood that a variety of modifications of the present invention which are different from the following embodiments may be implemented. However, in a description of the present invention, a detailed description of well-known functions or components of the related art will be omitted when it is deemed to obscure the essence of the present invention. Also, throughout the attached drawings, for promoting understanding of the present invention, some components may be exaggerated instead of being illustrated at actual scales thereof.

Although the terms first, second, and the like used herein may be used for describing a variety of components, the components are not limited to the terms. The terms are used only for distinguishing one component from another.

Also, the terms used herein are used merely for describing particular embodiments and are not intended to limit the scope of the present invention. Singular expressions, unless clearly defined otherwise in context, include plural expressions. Throughout the specification, the terms "comprise," "include," "consist of," and the like are used herein to specify the presence of stated features, numbers, stages, operations, elements, components or combinations thereof but do not preclude the presence or addition of one or more other features, numbers, stages, operations, elements, components, or combinations thereof.

Figure 1:
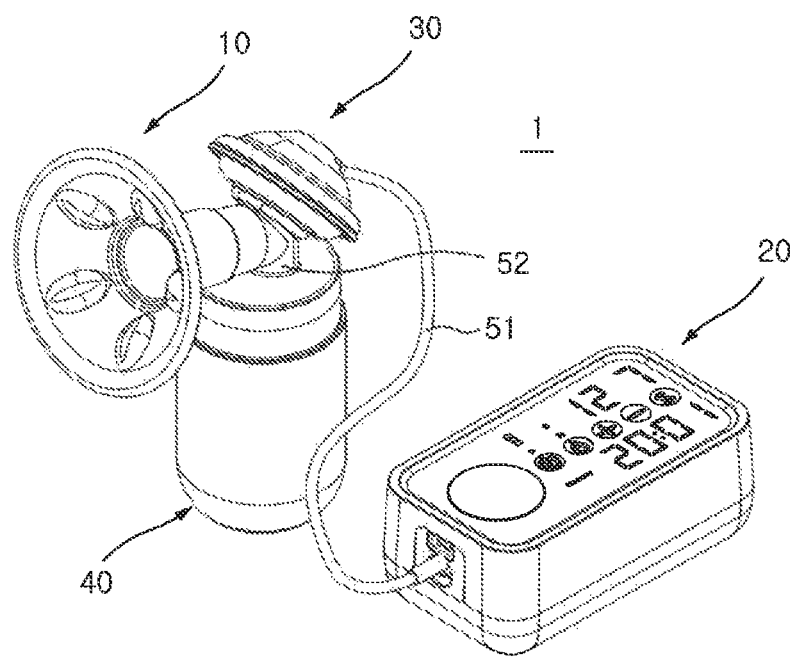
FIG. 1 is a perspective view of a breast pump according to one embodiment of the present invention.

FIG. 1 is a perspective view of a breast pump 1 according to one embodiment of the present invention. Referring to FIG. 1, the breast pump 1 according td one embodiment of the present invention includes a breast shield 10 worn on a breast of a woman, an airflow blocking portion 30 connected to the breast shield 10, a pumped milk storage portion 40 configured to store pumped mother milk, and a pressure adjustor 20 configured to adjust a pressure inside the breast shield 10.

The breast shield 10 is worn on a woman's breast. Here, when negative pressure is formed therein by the pressure adjustor 20, the breast shield 10 may be pressed against the woman's breast and applies the negative pressure to a nipple. When the negative pressure is applied to the nipple, breast milk may be pumped. The breast shield 10 will be described below in detail. Here, the term "woman's breast" may mean "woman's mamma."

The airflow blocking portion 30 may be connected to the pressure adjustor 20 by a connection tube 51, may allow a pressure transferred by the pressure adjustor to be effectively transferred to the breast shield 10, and selectively blocks air flow between the breast shield 10 and the pressure adjustor 20.

The pressure adjustor 20 may perform a function of forming negative pressure inside the breast shield 10 for pumping breast milk. To this end, the pressure adjustor 20 may include a piston (not shown) configured to adjust an air pressure, a cylinder (not shown), a motor (not shown) configured to drive at least one of the piston or the cylinder, and the like and is connected to the airflow blocking portion 30 through the connection tube 51.

The pumped milk storage portion 40 may be connected to the breast shield 10 through a connection pipe 52 so as to store pumped milk. The pumped milk flows out through the breast shield 10 and then is guided to the pumped milk storage portion 40 through the connection pipe 52.

Meanwhile, the connection pipe 52 may be connected to each of the airflow blocking portion 30, the breast shield 10, and the pumped milk storage portion 40. In this case, a guide plate (not shown) may be included in the breast shield 10 so as to guide the pumped milk from the breast shield 10 to the pumped milk storage portion 40 while simultaneously some air inside the breast shield 10 moves toward the pressure adjustor 20 through the airflow blocking portion 30 when negative pressure is formed by the pressure adjustor 20.

Figure 2:
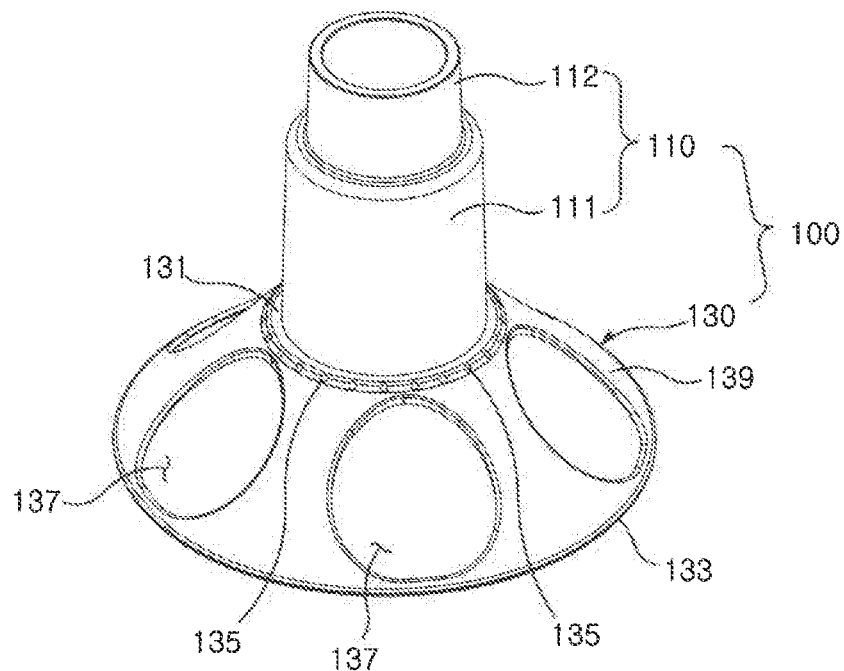
FIG. 2 is a perspective view illustrating a base portion of a breast shield shown in FIG. 1.

Hereinafter, the breast shield 10 will be described in detail with reference to FIGS. 2 and 3. FIG. 2 is a perspective view illustrating abase portion 100 of the breast shield 10 shown in FIG. 1, and FIG. 3 is a perspective view illustrating a soft portion 300 of the breast shield 10 shown in FIG. 1.

Figure 3:
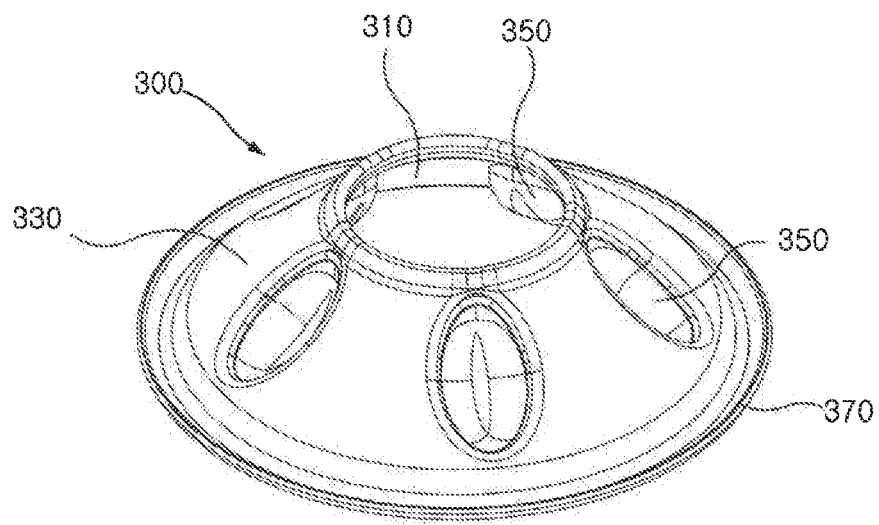
FIG. 3 is a perspective view illustrating a soft portion of a breast shield shown in FIG. 1.

Referring to FIGS. 2 and 3, the breast shield 10 is configured to pump breast milk from the woman's breast using negative pressure periodically changed by the pressure adjustor 20 and may be formed to be pressed against the woman's breast so as to partially accommodate the woman's breast therein. The breast shield 10 includes a parabolic cup or a funnel similar to a suction cup which is disposed over a part of a mamma and a nipple and is referred to as a mammary shield. The breast shield 10 generally may have a funnel shape to be pressed against the woman's breast but is not limited thereto.

The breast shield 10 may include abase portion 100 with stiffness. The base portion 100 may form a hollow in which the woman's breast can be accommodated. The breast shied 10 may include a soft portion 300 configured to surround the base portion 100.

Since the base portion 100 is formed of a hard material, even when negative pressure is transferred thereinside by the pressure adjustor 20, a change in shape is minimized so as to easily transfer the negative pressure to the human's breast.

The base portion 100 may include the hollow formed therein and includes both ends and a sidewall 139 extending from any one of the both ends toward the other so as to define the hollow. The both ends of the base portion 100 are open such that the hollow communicates with the outside of the base portion 100. The human's breast may be allowed to pass through any one of the both ends of the base portion 100 and be accommodated in the hollow. Meanwhile, the base portion 100 may include one or more through holes 137 passing through the sidewall 139.

The base portion 100 may have a shape in which a sectional area gradually increases from one end toward the other end of the both ends in order to effectively transfer the negative pressure to the human's breast. In this case, the human's breast is inserted through the other end having a greater sectional area.

The base portion 100 may have a funnel shape with open both ends and a hollow therein. The funnel has a sectional area gradually increasing from one end toward the other end and is appropriate for accommodating the human's breast.

Meanwhile, the base portion 100 may further include a pipe portion 110. In this case, the base portion 100 includes the pipe portion 110 and an extending portion 130 connected to the pipe portion 110 to communicate therewith. The extending portion 130 may be worn on the human's breast in a way that the human's breast may be accommodated therein.

The extending portion 130 may include a hollow therein and a first end portion 131, a second end portion 133 having a greater sectional area than that of the first end portion 131, and the sidewall 139 which connects the first end portion 131 and the second end portion 133 to each other.

The first end portion 131 and the second end portion 133 may be open so as to allow the hollow to communicate with the outside. The first end portion 131 may be connected to the pipe portion 110 and allows an internal space of the pipe portion 110 to communicate with the hollow. The second end portion 133 may have an appropriate sectional area such that the human's breast passes therethrough to be accommodated in the hollow.

The sidewall 139 of the extending portion 130 may form the above-described sidewall 139 of the base portion 100, may be formed to be inclined with respect to a longitudinal direction of an end portion, and includes the one or more through holes 137 which allow the outside and inside of the extending portion 130 to communicate with each other.

Meanwhile, a plurality of coupling holes 135 may be provided at an outer surface of the first end portion 131 of the extending portion 130 along a perimeter of the first end portion 131. Parts of a surface of the soft portion 300 which will be described below are inserted into the coupling holes 135 so as to prevent the soft portion 300 from moving along a surface of the base portion 100, that is, the extending portion 130.

The pipe portion 110 may include a space therein and allow some air inside the breast shield 10 to be movable to the pressure adjustor 20 through the pipe portion 110 when negative pressure is formed by the pressure adjustor 20. The pipe portion 110 may be provided as a single member but may include a first pipe portion 111 connected to the first end portion 131 of the extending portion 130 and a second pipe portion 112 connected to the first pipe portion 111. The sectional area of the second pipe portion 112 may be smaller than the sectional area of the first pipe portion 111.

The soft portion 300 may be formed of a flexible material and has flexibility. The soft portion 300 may be formed to surround an outer surface and inner surface of the base portion 100. Accordingly, the soft portion 300 may prevent airflow through the through holes 137 by blocking the through holes 137.

The soft portion 300 may include a first soft layer 310 pressed against the inner surface of the base portion 100, a second soft layer 330 pressed against the outer surface of the base portion 100, and a third soft layer 350 provided in each of the through holes 137.

The first soft layer 310 may be provided inside the base portion 100, that is, the extending portion 130 and is pressed against an inner surface of the extending portion 130. The first soft layer 310 may be referred to as an internal soft layer.

The second soft layer 330 may be provided outside the base portion 100, that is, the extending portion 130, and is pressed against an outer surface of the extending portion 130. The second soft layer 330 may be referred to as an external soft layer.

The third soft layer 350 may be provided in the through hole 137 and includes an edge connected to each of the first soft layer 310 and the second soft layer 330. When negative pressure is formed in the base portion 100, that is, the extending portion 130, the third soft layer 350 elongates with parts of the first soft layer 310 and the second soft layer 330 connected to the edge and move toward the inside of the extending portion 130. The third soft layer 350 which has moved pressurizes and stimulates the human's breast. Mammary glands of the pressurized breast, that is, a woman's mamma, are massaged so as to easily pump breast milk.

The third soft layer 350 may be previously formed to be convex toward the inside of the extending portion 130 in order to move deep inside and to stimulate the breast while elongating due to the negative pressure. In this case, the third soft layer 350 may also adequately elongate due to negative pressure at a low level.

Accordingly, the soft portion 300 may include a single layer area covering the through holes 137 and a double layer area connected to the single layer area and configured to accommodate the base portion 100 therein.

Meanwhile, the soft portion 300 may further include a contact edge 370 provided along an end of the extending portion 130, that is, an edge of the second end portion 133.

The contact edge 370 may be formed to be pressed against the human's breast and maintains sealing between the human's breast and the contact edge 370. Accordingly, when the breast shield 10 is pressed against the breast, air does not flow into the breast shield 10 through a contact part.

The contact edge 370 may be formed to be convex toward the breast to be pressed against the breast. As an example, the contact edge 370 is formed to be inclined downward to become farther from a center of the soft portion 300 in a radial direction and then be inclined upward at a certain curvature to become farther from the center of the soft portion 300 in the radial direction.

Here, "downward" is a direction from a center toward a bottom end of FIG. 3 and "upward" is a direction from the center toward a top end of FIG. 3.

The contact edge 370 may be connected to the first soft layer 310 and the second soft layer 330.

The soft portion 300 may be formed through insertion molding by inserting the base portion 100 into a mold (not shown). When the soft portion 300 is formed through insertion molding, a high-temperature melted resin or the like is easily inserted into the coupling holes 135.

Meanwhile, the second soft layer 330 may be omitted in the soft portion 300. In this case, the first soft layer 310 and the third soft layer 350 are connected to each other. The first soft layer 310 may be welded and bonded to the inner surface of the base portion 100, that is, the inner surface of the extending portion 130 using ultrasonic waves. Ultrasonic welding is a phenomenon in which the resin forming the soft portion 300 is heated, softened, and melted by ultrasonic oscillation.

Ultrasonic bonding does not need an adhesive or solvent, may have a very fast welding speed, and does not cause a change or damage on a surface of a welded material. Due to strong welding, high degrees of water-tightness and air-tightness are provided, and there is no need for pre-treatment or post-treatment, a working environment is clean, and production efficiency is improved.

Figure 4:
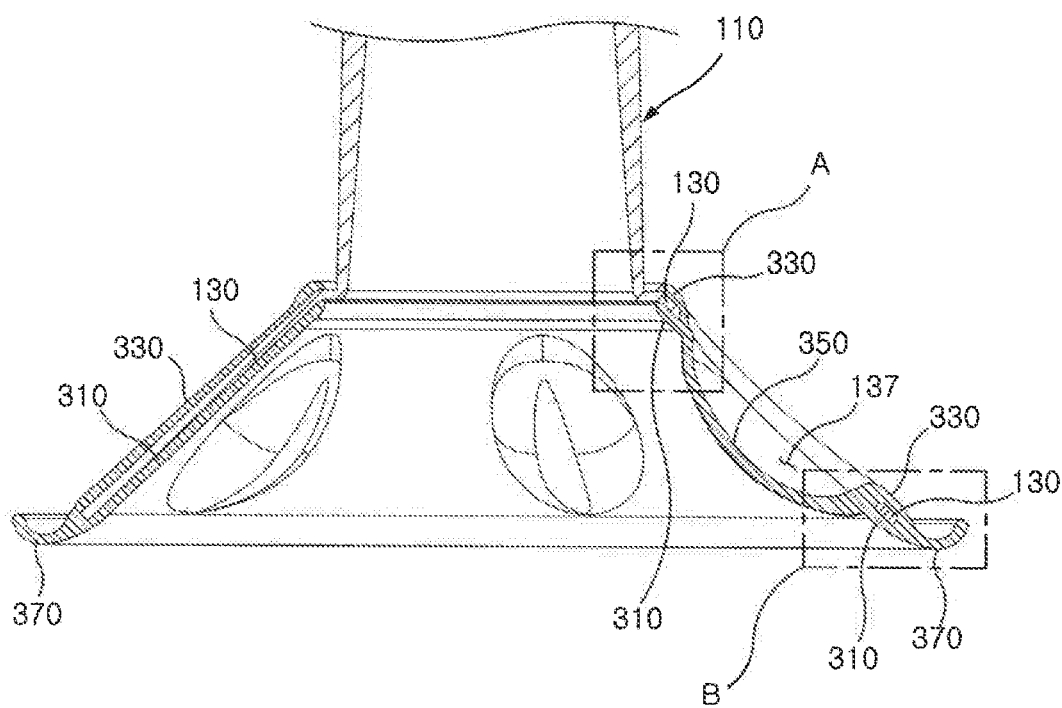
FIG. 4 is a cross-sectional view illustrating a state in which the base portion and the soft portion of the breast shield shown in FIG. 1 are coupled with each other.

Hereinafter, an operation of the soft portion 300 of the breast shield 10 will be described with reference to FIGS. 4 to 6. FIG. 4 is a cross-sectional view illustrating a state in which the base portion 100 and the soft portion 300 of the breast shield 10 shown in FIG. 1 are coupled with each other, FIG. 5 is an enlarged view illustrating area A of FIG. 4, and FIG. 6 is an enlarged view illustrating area B of FIG. 4.

Figure 5:
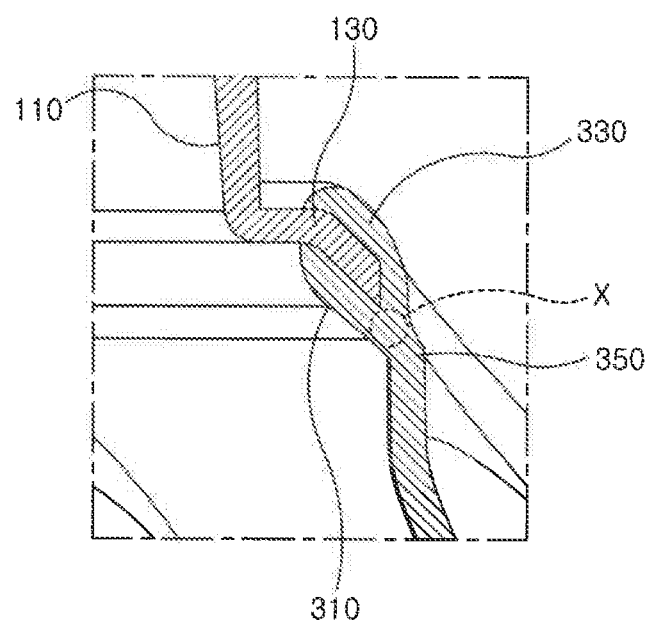
FIG. 5 is an enlarged view illustrating area A of FIG. 4.
Figure 6:
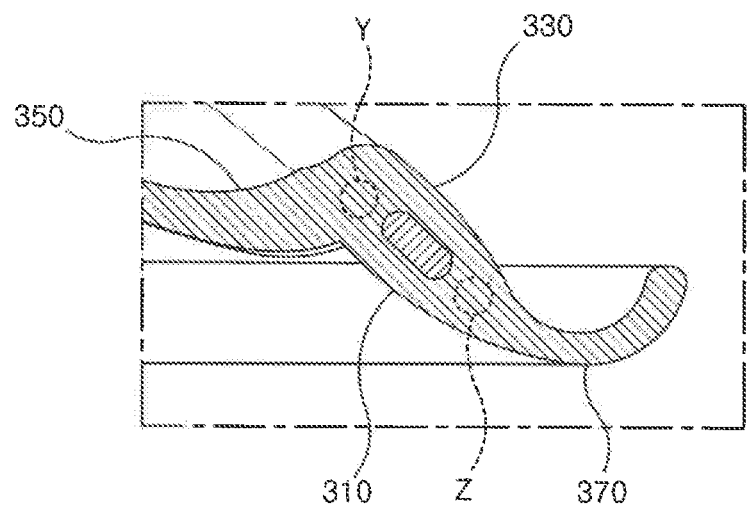
FIG. 6 is an enlarged view illustrating area B of FIG. 4.

Referring to FIGS. 4 to 6, the outer surface of the extending portion 130 may come into contact with the second soft layer 330 and the inner surface thereof comes into contact with the first soft layer 310. Also, the extending portion 130 may be in a state in which the through holes 137 may be blocked by the third soft layer 350. Here, when the negative pressure formed by the pressure adjustor 20 may be transferred to the inside of the breast shield 10, that is, the extending portion 130, the third soft layer 350 elongates and starts moving toward the inside of the extending portion 130.

In related arts, the second soft layer 330 may be not provided. Accordingly, when the third soft layer 350 elongates and moves to the inside, a change may occur in while the soft portion 300 shrinks due to the negative pressure such that the first soft layer 310 is spaced apart from the inner surface of the extending portion 130.

When such a gap occurs, the inside of the extending portion 130 may communicate with the outside. Accordingly, outside air may flow thereinto such that a level of internal negative pressure is reduced and additionally breast milk thereinside is discharged outward.

In the breast shield 10 according to one embodiment of the present invention, since the second soft layer 330 pressed against the outer surface of the extending portion 130 is coupled with the first soft layer 310, even when the third soft layer 350 elongates and moves toward the inside, the first soft layer 310 is not spaced apart from the extending portion 130.

Referring to FIG. 5, the first soft layer 310, the second soft layer 330, and the third soft layer 350 of the soft portion 300 may be connected to one another through area X adjacent to the first end portion 131 of the extending portion 130.

When the third soft layer 350 elongates and moves toward the inside of the extending portion 130, the first soft layer 310 may receive a force directed toward the inside of the extending portion 130 through the area X. The force directed toward the inside the extending portion 130 may be a force applied to space the first soft layer 310 apart from the inside of the extending portion 130.

Although the area X is connected to the third soft layer 350 and receives the force directed toward the inside of the extending portion 130, movement directed toward the inside of the extending portion 130 may be minimized by the second soft layer 330. This is because movement of the second soft layer 330 is minimized by a frictional force between the second soft layer 330 and the outer surface of the extending portion 130 such that movement of the area X is also minimized.

That is, although the second soft layer 330 receives a force in a direction approximately parallel to the surface of the extending portion 130 from the third soft layer 350 through the area X, moving toward the area X may be blocked by a frictional force caused by rubbing against the surface of the extending portion 130.

In this case, when a part of the second soft layer 330 is inserted into the coupling hole 135, the frictional force may be further increased.

Accordingly, since the first soft layer 310 is connected to and supported by the area X, the first soft layer 310 can be changed, for example, shrinks toward the inside of the extending portion 130, and is minimally spaced apart from the inner surface of the extending portion 130.

Referring to FIG. 6, the soft portion 300 may include area Y and area Z adjacent to the second end portion 133 of the extending portion 130. The first soft layer 310, the second soft layer 330, and the third soft layer 350 of the soft portion 300 may be connected to one another through the area Y, and the first soft layer 310, the second soft layer 330, and the contact edge 370 may be connected to one another through the area Z.

Likewise, when the third soft layer 350 elongates and moves toward the inside of the extending portion 130, since the first soft layer 310 is connected to and supported by the area Y due to the same principle, the first soft layer 310 may be minimally spaced apart from the inner surface of the extending portion 130. Here, movement of the area Y may be minimized by a frictional force between the second soft layer 330 and the outer surface of the extending portion 130.

Meanwhile, since the first soft layer 310 is connected to and supported by the area Z, the first soft layer 310 may be minimally spaced apart from the inner surface of the extending portion 130. Here, a force of minimizing movement of the area Z may include not only the frictional force between the second soft layer 330 and the outer surface of the extending portion 130 but also a frictional force between the contact edge 370 and the breast.

Operations of the breast pump 1 according to one embodiment of the present invention will be described with reference to FIGS. 1 to 6.

First, the breast shield 10 is worn on a human's breast. When the breast shield 10 is worn thereon, the human's breast, that is, a woman's mamma, is accommodated in the breast shield 10.

The contact edge 370 is pressed against the breast or a part near the breast so as to prevent air from flowing into through a contact part.

When the pressure adjustor 20 operates, negative pressure is generated.

When the negative pressure is generated, air in the breast shield 10, that is, the extending portion 130, moves outward through the pipe portion 110 and pumping of breast milk is started.

When pumping of breast milk is started, the breast milk is stored in the pumped milk storage portion 40.

In this case, negative pressure is also formed in the breast shield 10, that is, the extending portion 130. Since the first soft layer 310 is supported by the area X, the area Y, and the area Z, even when the negative pressure is formed, the first soft layer 310 is not spaced apart from the inner surface of the extending portion 130.

Although one embodiment of the present invention has been described above with reference to the drawings, the present invention is not limited thereto and it is apparent that a variety of changes and modifications may be made by one of ordinary skill in the art without departing from the technical scope of the present invention and the following claims.

BRIEF DESCRIPTION OF REFERENCE NUMERALS

1: breast pump
100: base portion
110: pipe portion
130: extending portion
135: coupling hole
300: soft portion
310: first soft layer
330: second soft layer
350: third soft layer
370: contact edge

The invention claimed is:

1. A breast shield (10) used in a breast pump, said breast pump configured to pump human breast milk, the breast shield (10) comprising:
 a base portion (100) including a pipe portion (110) and an extending portion (130), wherein a hollow is formed in the base portion (100), the extending portion (130) including a first end portion (131) connected to the pipe portion (110), a second end portion (133) having a greater circumferential cross-sectional area than the first end portion (131) and a sidewall (139) connecting the first end portion (131) and the second end portion (133), the first end portion (131) and the second end portion (133) being open, and the extending portion (130) being configured to accommodate a part of a human breast in the hollow through the second end portion (133) wherein the extending portion (130) is provided with through holes (137), passing through the sidewall (139) of the extending portion (130); and
 a soft portion (300), surrounding an entire outer surface and an entire inner surface of the extending portion (130), preventing airflow through the through holes (137), and having flexibility,
 wherein the soft portion (300) comprises:
  a first soft layer (310), being pressed against the entire inner surface of the extending portion (130) except for the through holes (137);
  a second soft layer (330) being pressed against the entire outer surface of the extending portion (130) except for the through holes (137); and
  a third soft layer (350), being provided as a single layer at the through holes (137), being connected to both the first soft layer (310) and the second soft layer (330) only at an edge of each of the through holes (137), being convex by going through the through holes (137) toward an inside of the extending portion (130).

2. The breast shield (10) of claim 1, wherein the third soft layer (350) elongates and moves toward the inside of the extending portion (130) when negative pressure is formed in the base portion (100).

3. The breast shield (10) of claim 1, wherein the soft portion (300) is formed through insertion molding.

4. A breast pump (1) comprising:
 a breast shield (10) configured to be pressed against a human's breast;
 a pressure adjustor (20) being configured to adjust pressure inside the breast shield (10) to pump human breast milk; and
 a pumped milk storage portion (40), storing the pumped human breast milk,
 wherein the breast shield (10) comprises:
  a base portion (100), having a funnel shape including open both ends, a pipe portion (110), an extending portion (130), and a hollow in the base portion, wherein the extending portion (130) includes a first end portion (131) connected to the pipe portion (110), a second end portion (133) having a greater circumferential cross-sectional area than the first end portion (131), and a sidewall (139) connecting the first end portion (131) and the second end portion (133), wherein the extending portion (130) is provided with through holes (137) passing through the sidewall (139) of the extending portion (130); and
  a soft portion (130), having flexibility, and including a single layer area (350) covering the through holes (137), a double layer area comprising an inner layer (310) and an outer layer (330) which are connected to the single layer area (350) only at an edge of each of the through holes (137),
 wherein the double layer area accommodates the extending portion (130), the inner layer (310) presses against an entire inner surface of the extending portion (130) except for the through holes (137), the outer layer (330) presses against an entire outer surface of the extending portion (130) except for the through holes (137), and the single layer area (350) is convex by going through the through holes (137) toward an inside of the extending portion (130).

* * * * *